United States Patent [19]

Ribier et al.

[11] Patent Number: 5,629,015

[45] Date of Patent: *May 13, 1997

[54] COMPOSITION FOR COMBATING AGEING ACTING SIMULTANEOUSLY ON THE SURFACE LAYERS AND DEEP LAYERS OF THE SKIN AND USE THEREOF

[75] Inventors: Alain Ribier; Jean-Thierry Simonnet; Florence Girerd, all of Paris; Francoise Gagnebien-Cabanne, Chatillon, all of France

[73] Assignee: L'Oreal, Paris, France

[ * ] Notice: The term of this patent shall not extend beyond the expiration date of Pat. No. 5,614,215.

[21] Appl. No.: 366,740

[22] Filed: Dec. 30, 1994

[30] Foreign Application Priority Data

Dec. 30, 1993 [FR] France .................. 93 15867

[51] Int. Cl.⁶ .................. A61K 9/127; A61K 7/00
[52] U.S. Cl. .................. 424/450; 424/401; 514/844
[58] Field of Search .................. 428/402.2; 424/450, 424/401, 62; 514/844

[56] References Cited

U.S. PATENT DOCUMENTS 5,422,120  6/1995  Kim .................. 424/450

FOREIGN PATENT DOCUMENTS 0559502  9/1993  European Pat. Off. .
2408387  6/1979  France .
WO9315708  8/1993  WIPO .

OTHER PUBLICATIONS

International Journal of Pharmaceutics, vol. 62, No.1, 1990, NL, pp. 75–79, Gagrijelcic et al., "Evaluation of liposomes as drug carriers into the skin by one-dimensional epr imaging," * entire document*.

Soap, Cosmetics, Chemical Specialities, vol. 69, No. 7, Jul. 1993, p. 77 "Formulation ideas," *liposome eye treatment*.

Primary Examiner—Gollamudi S. Kishore
Attorney, Agent, or Firm—Oblon, Spivak, MClelland, Maier & Neustadt, P.C.

[57] ABSTRACT

Compositions comprising a first dispersion of lipid vesicles which are capable of penetrating into the deep layers of the skin and which contain at least one active agent chosen from moisturizing agents, anti-free-radical agents, keratolytic agents, protides, enzymes, anti-elastase agents and anti-collagenase agents, and fatty acid derivatives, for treating these deep layers, and a second dispersion of lipid vesicles which are capable of penetrating into the surface layers of the skin and which contain at least one active agent chosen from keratolytic agents, tensioning agents, moisturizing agents, surface-restructuring agents and anti-free-radical agents, for treating these surface layers, are effective for combating ageing, acting simultaneously on the surface layers and deep layers of the skin.

17 Claims, No Drawings

COMPOSITION FOR COMBATING AGEING ACTING SIMULTANEOUSLY ON THE SURFACE LAYERS AND DEEP LAYERS OF THE SKIN AND USE THEREOF

BACKGROUND OF THE INVENTION

1. Field of the Invention

The present invention relates to compositions for the cosmetic or dermatological treatment of imperfections or complaints of the skin, including the scalp. It relates more particularly to a composition for combating ageing, comprising at least one active agent which is conveyed via at least two distinct types of lipid vesicles. The present invention also relates to the use of this composition for combating ageing of the skin, and to a method for combating the ageing of the skin by applying such a composition to the skin.

2. Discussion of the Background

Many examples are known of cosmetic or dermatological compositions intended for treating the skin, which have one or more active agents that are suitable for treating the skin and which are encapsulated in lipid spherules or vesicles (also known an liposomes).

Lipid spherules or vesicles are understood to refer to particles formed of a membrane consisting of one or more concentric lamellae, these lamellae containing one or more bimolecular layers of amphiphilic lipids encapsulating an aqueous phase. The aqueous phase may contain water-soluble active substances, and the bimolecular layers of amphiphilic lipids may contain lipophilic active substances.

These spherules generally have a mean diameter of between 10 nm and 5000 nm. Among the many documents published regarding this matter, there may be mentioned the French Certificate of Addition 2,408,387 which describes a composition based on aqueous dispersions of ionic or non-ionic lipid spherules encapsulating at least one active substance. More precisely, this document describes compositions containing at least two dispersions of spherules containing different active agents, for the purpose of obtaining a mixed system, that is to say a system in which a first dispersion of spherules containing a first type of active substance is combined with a second dispersion of spherules containing another type of active substance, which enables the two types of substances to act simultaneously at the time of treatment and possibly to obtain a synergic effect which would not be produced if these two types of substances were made to act successively and separately.

It is known that during the ageing process various signs which are very characteristic of this ageing appear on the skin, reflected especially in a modification of the cutaneous structure and function. This ageing is physiological in nature but is also photo-induced, that is to say that it is due to the repeated exposure of the skin to light and, consequently, to the formation of oxygenated free radicals via the action of this light on the constituents of the skin.

The main clinical signs of cutaneous ageing are especially the following: appearance of deep wrinkles which increase with age. In particular, disruption of the "grain" of the skin in observed, that in to say that the microrelief is less uniform and is anisotropic in nature.

Moreover, the skin complexion is generally modified; it appears paler and yellower, which appears to be due essentially to disruption of the microcirculation (less haemoglobin in the dermal capillaries). Many colored blemishes appear at the skin surface, due to impaired melanogenesis. Diffuse irritations, and sometimes telangiectasia, occur in certain areas.

Another clinical sign of ageing is the dry and rough appearance of the skin, which is essentially due to a more considerable desquamation; by diffracting light rays, these squama also contribute towards the somewhat grey appearance of the complexion.

Finally, a loss of firmness and of tonicity of the skin are observed which, as for wrinkles, is at least partly explained by a dermal and epidermal atrophy and a flattening out of the dermoepidermal formation.

It is thus observed that the clinical signs of cutaneous ageing result essentially from a dysfunction of the main biological mechanisms involved in the skin.

It is well known that the skin consists of surface layers, the stratum corneum, and of deep layers, the live epidermis and the dermis. However, specific delivery of such an active agent into the surface layers and, simultaneously, of the same or another active agent into the deep layers, was not known from the prior art.

Thus, there remains a need for a method of combating the aging of the skin which simultaneously acts on the surface layers and the deep layers of the skin. There also remains a need for compositions useful in such methods.

SUMMARY OF THE INVENTION

Accordingly, it is one object of the present invention to provide a novel method for combating the aging of skin.

It is another object of the present invention to provide a method for combating the aging of skin which simultaneously acts on the surface layers and deep layers of skin.

It is another object of the present invention to provide novel compositions useful in such methods.

These and other objects, which will become apparent during the following detailed description, have been achieved by the inventors' discovery that compositions comprising:

(a) a first dispersion of lipid vesicles which are capable of penetrating into the deep layers of the skin and which contain at least one active agent chosen from moisturizing agents, anti-free-radical agents, keratolytic agents, protides, enzymes, anti-elastase agents and anti-collagenase agents, and fatty acid derivatives, for treating these deep layers; and (b) a second dispersion of lipid vesicles which are capable of penetrating into the surface layers of the skin and which contain at least one active agent chosen from keratolytic agents, tensioning agents, moisturizing agents, surface-restructuring agents and anti-free-radical agents, for treating these surface layers, are effective for combating aging and simultaneously act on the surface layers and deep layers of the skin.

Thus, the inventors have now developed cosmetic and/or dermatological compositions for combating ageing, which allow the simultaneous action of two different active agents, and which furthermore allow these active agents to act in different areas of the skin, that is to say in the surface layers and in the deep layers of the skin, thereby very markedly enhancing the effectiveness of these compositions and the complementary or synergic effect of the anti-ageing active agents used.

The inventors have also developed cosmetic or dermatological compositions for combating ageing, which enable the same active agent to act simultaneously in the surface layers and in the deep layers of the skin, providing a more complete and therefore a more effective treatment of the disorder from which it is suffering.

The composition according to the invention relates equally well to combating the appearance of ageing, to combating existing age marks, such as wrinkles, and to protecting the skin against light radiation.

Thus, the compositions according to the present invention are capable of treating already existing wrinkles, of preventing ageing of the skin and of protecting it, by suppressing the formation of free radicals.

According to a specific embodiment, the active agents contained in the first dispersion of vesicles and in the second are the same.

DETAILED DESCRIPTION OF THE PREFERRED EMBODIMENTS

The Applicant has used a means of classifying vesicles which enables a person skilled in the art readily to select lipid vesicles capable of conveying the active agent to the deep layers of the skin, known an vesicles with deep-down action, and those capable of conveying the active agent to the surface layers of the skin, known as vesicles acting at the surface.

This classification is made on the basis of the diffusion constant D of a probe introduced into the vesicles. This probe is N-(1-oxyl-2,2,6,6-tetramethyl-4-piperidyl)-N,N-dimethyl-N-hydroxyethylammonium iodide, ASL, of formula (I):

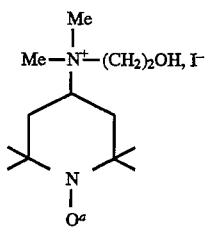

Vesicles for which the diffusion constant D of the probe into the stratum corneum is $>1\times 10^{-7}$ cm$^2$ $^{-1}$ are vesicles which are capable of penetrating into the deep layers of the skin.

Vesicles for which the diffusion constant D of the probe into the stratum corneum is $<1\times 10^{-7}$ cm$^2$ s$^{-1}$ are vesicles which are capable of conveying the active agent to the surface layers of the skin.

The vesicles of the first type, the so-called vesicles with deep-down action, are generally in the fluid state at room temperature (about 20° C.), and those of the second type, the so-called vesicles acting at the surface, are generally in the gelled state at room temperature. The means of recognizing the state of the vesicles consists in determining the phase (fluid-gel lamellar) transition temperature of the main lipid constituting the membrane thereof, by differential thermal analysis (DTA).

Other characteristics of these vesicles relate to their ability to deliver the active agent to a greater or lesser depth in the skin. This is particularly the case for the degree of encapsulation.

Glucose is a labelling agent conventionally used for this type of determination (see in particular, *Liposomes a practical approach* by R. R. C. New, IRL Press, pp. 125–136 (1990)).

The degree of encapsulation is expressed an the volume of glucose solution encapsulated in the vesicles, measured in μl relative to the unit weight (mg) of the lipids constituting the membrane. This degree of encapsulation is determined immediately after the step of separation of the free glucose from the encapsulated glucose ($T_0$), as well as twenty-four hours after this separation ($T_{24}$ hours).

The difference between these two successive determinations illustrates the permeability of the vesicles with respect to the encapsulated glucose, which may also be referred to as their encapsulation potential.

The first type of vesicles (delivering the active agent into the deep layers of the skin) has a high encapsulation potential for the small water-soluble molecules which are conventionally modelled by glucose, this encapsulation potential being maintained for at least 24 hours. The second type of vesicles (delivering the active agent into the surface layers of the skin) does not retain glucose in the encapsulated state for the same amount of time.

The main lipids constituting the vesicles of the first type (deep delivery of the active agent) are composed of at least one linear and saturated fatty chain of length ranging from 16 to 30 carbon atoms, such an hydrogenated phospholipids (from plants or from egg), saturated synthetic phospholipids such as dipalmitoylphosphatidylcholine, and polyol alkyl ethers or polyol alkyl esters containing one, two or three fatty chains per molecule. These lipide are used alone or as a mixture.

The main lipids constituting the vesicles of the second type (active agent delivered at the surface) are chosen in particular from the group comprising ionic lipids, especially such as natural plant- or egg-based phospholipids, containing unsaturated fatty chains having from 16 to 30 carbon atoms; nonionic lipids such an polyol alkyl ethers or polyol alkyl esters composed of one or more fatty chains per molecule, including at least one fatty chain with a length of less than 16 carbon atoms, such as lauryl polyglyceryl-6-cetearyl glycol ether, described in detail in French Patent Application FR 92-09603 filed by L'Oréal.

It is possible, in a known manner, to incorporate into the lipid phase constituting the lipid membrane of the vesicles, at least one additive chosen from the group formed of sterols (phytosterols, cholesterol or polyoxyethylenated phytosterols); long-chain alcohols, diols and triols (phytanetriol), long-chain amines and the quaternary ammonium derivatives thereof; phosphoric esters of fatty alcohols and the alkali metal (Na or K) salts thereof, such an dicetyl phosphate, sodium dicetyl phosphate, alkyl sulfates (sodium cetyl sulfate), alkali metal salts of cholesterol sulfate or of cholesterol phosphate, the sodium salt of phosphatidic acid, and lipoamino acids and the salts thereof, such as the sodium acylglutamates.

Examples of vesicles of the first type (delivering the active agent into the deep layers of the skin) which may be mentioned are Vesicles obtained from the following lipids (CTFA name):

A/cholesterol/casein lipoamino acid, especially in a 45/45/10 weight ratio (where A is a triglyceryl cetyl ether marketed by the company Chimex under the name Chimexane NL);

B/cholesterol/dicetyl phosphate, especially in a 60/35/5 weight ratio (where B is a mixture of triglyceryl mono-, di- and tricetyl ether, marketed by the company Chimax under the name Chimexane NT);

Span 40 (from ICI, or Sorbitan palmitate)/cholesterol/sodium acylglutamate (marketed under the name HS11 by the company Ajinomoto), especially in a 47.5/47.5/5 weight ratio;

PEG 8 stearate/cholesterol/sodium acylglutamate, especially with a 47.5/47.5/5 weight ratio (where PEG 8 stearate is polyethylene glycol containing 8 units of ethylene oxide, marketed by the company Unichema under the name PEG 400 stearate);

PEG 8 stearate/cholesterol/phytanetriol/sodium acylglutamate, especially with a 47.5/20/27.5/5 weight ratio;

Hydrogenated lecithin/polyoxyethylenated phytosterol containing 5 units of ethylene oxide, especially in a 60/40 weight ratio;

Polyoxyethylenated methylglucose distearate containing 20 units of ethylene oxide/cholesterol/sodium acylglutamate, especially in a 45/45/10 weight ratio (the distearate being, for example, that sold under the name Glucam E 20 distearate by Amerchol);

A/cholesterol/dicetyl phosphate, especially with a 47.5/47.5/5 weight ratio;

Diglyceryl distearate (for example that sold by Nihon under the name Emalex DS G2)/cholesterol/sodium acylglutamate, in a 45/45/10 weight ratio;

Sucrose mono- and distearate (for example that sold by Grillo under the name Grilloten PSE 141 G)/cholesterol/sodium acylglutamate, especially in a 45/45/10 weight ratio;

Tetraglyceryl tristearate (for example that sold by Nikkol under the name Tetraglyn 3S)/cholesterol/sodium acylglutamate, especially in a 45/45/10 weight ratio.

Examples of vesicles of the second type (delivering the active agent into the surface layers of the skin) which may be mentioned are vesicles obtained from the following lipids:

Sunflower lecithin;

Natipide II (soya lecithin/ethanol/water in a 20/16/64 weight ratio, marketed by Nattermann);

C (soya lecithin/cholesterol/propylene glycol in a 60/20/20 weight ratio, marketed by Nattermann under the name NAT 50 PG);

D/dimyristyl phosphate, especially in a 95/5 weight ratio (where D is a lauryl polyglyceryl-6-cetearyl glycol ether marketed by the company Chimax under the name Chimexane NS).

Table I below gives, for some of the vesicles obtained using the above lipids, the diffusion constant D for ASL in the stratum corneum and in the epidermis/dermis, as well as the degree of encapsulation of glucose and the phase transition temperature of the main lipid constituting the membrane. The diffusion constant was measured for an encapsulated ASL concentration of 0.35% by weight based on the total weight of the composition.

TABLE I

| Ref. | LIPID SYSTEMS | Proportions % by weight (mg) | Diffusion coefficient D in $10^{-7}$ cm$^2$ s$^{-1}$ | | Degree of encapsulation of glucose in µl/mg | | Phase transition temperature in °C. |
|---|---|---|---|---|---|---|---|
| | | | in the stratum corneum | in the epidermis/ dermis | $T_o$ | $T_{24h}$ | |
| | 1st type - deep down | | | | | | |
| 1 | A/cholesterol/casein lipoamino acid | 45/45/10 (67.5/67.5/15) | 42 | 5 | 7.5 | 6.8 | 50 |
| 2 | B/cholesterol/dicetyl phosphate | 60/35/5 (90/52.5/7.5) | 58 | 2 | 11.1 | 11.1 | 54 |
| 3 | Span 40/cholesterol/ sodium acylglutamate | 47.5/47.5/5 (71.25/71.25/7.5) | 42 | 2 | 13.8 | 13.8 | 50 |
| 4 | PEG 8 stearate/ cholesterol/sodium acylglutamate | 47.5/47.5/5 (71.25/71.25/7.5) | 42 | 2 | 14.4 | 14.4 | 55 |
| 5 | PEG 8 stearate/ cholesterol/phytanetriol/ sodium acylglutamate | 47.5/20/27.5/5 (71.25/30/ 41.25/7.5) | 8.3 | 2.5 | 4.1 | 3.0 | 55 |
| 6 | Hydrogenated lecithin/ polyoxyethylenated phytosterol | 60/40 (90/60) | 8 | 2 | 6.0 | 4.8 | 80 |
| | 2nd type - surface | | | | | | |
| 7 | Sunflower lecithin | 100 (150) | 0.3 | 0.2 | 1.6 | 0 | <0 |
| 8 | Natipide II (soya lecithin/ethanol/water) | 20/16/64 (30/24/96) | 0.4 | 0.2 | 0.4 | 0 | <0 |
| 9 | C (soya lecithin/ sterols/propylene glycol) | 60/20/20 (90/30/30) | 0.25 | 0.1 | 1.8 | 0 | <0 |
| 10 | D/dimyristyl phosphate | 95/5 (142.5/7.5) | 0.3 | 0.2 | 2.0 | 0 | 14 |

Measurement of the diffusion constant D is carried out by combining two methods using a paramagnetic probe, ASL: one-dimensional and periodic electron paramagnetic resonance (EPR), on the one hand, and EPR kinetic imaging, on the other hand. These two methods are respectively described in the articles "Evaluation of liposomes as drug carriers into the skin by one-dimensional EPR imaging" by V. Gabrijelcic et al., *International Journal of Pharmaceutics*, vol. 62, pp. 75–79, Elsevier (1990), and "Liposome entrapped molecules penetration into the skin measured by nitroxide reduction kinetic imaging" by V. Gabrijelcic et al., *Periodicum Biologorum*, vol. 93, No. 2, pp. 245–246 (1991).

Measurement of the degree of encapsulation in carried out as described in *Liposomes a practical approach*, by R. R. C.

New, IRL Press, pp. 125–136 (1990) cited above, and that of the phase transition temperature is carried out an described above.

Advantageously, several active agents are used simultaneously in each type of vesicles, these active agents having the same function and/or imparting to the skin, at the surface and deep down, the same type of effect; the agents active at the surface and the agents with deep-down action are thus complementary.

The active agents with deep-down action and the agents active at the surface which may be used in the invention are those which are conventionally used in the cosmetic or dermatological field.

The active agents with deep-down action are chosen from moisturizing agents, anti-free-radical agents, keratolytic agents, protides, fatty acid derivatives, enzymes, anti-elastase agents and anti-collagenase agents.

Examples of moisturizing agents which may be mentioned are sodium lactate, polyols and in particular glycerine, mannitol and amino acids.

Agents involved in an anti-free-radical action which may be mentioned are phosphonic acid derivatives, ethylenediaminetetraacetic acid and the salts thereof such as the sodium salt, guanosine, superoxide dismutase, tocopherol (vitamin E) and the derivatives thereof (acetate), ethoxyquin, lactoferrin, lactoperoxidase and nitroxide derivatives.

Keratolytic agents with deep-down action which may be mentioned are α-hydroxy acids derived from fruit, such as glycolic acid, lactic acid, citric acid, mandelic acid and mixtures thereof; salicylic acid derivatives such an 5-n-octanoylsalicylic acid or 5-n-dodecanoylsalicylic acid; retinol (vitamin A) and derivatives thereof.

Protides which may be mentioned are peptide derivatives and proteins (from wheat or from soya) and the hydrolyzates thereof. Fatty acid derivatives which may be mentioned are polyunsaturated phospholipids, including the essential fatty acid phospholipids from octopus.

Anti-elastase agents which may be mentioned are peptides from legume needs, such an those marketed by the Laboratoires Sériabiologiques, Nancy under the reference Parelastyl. Anti-collagenase agents which may be mentioned are metalloprotease inhibitors such an ethylenediaminetetraacetic acid (EDTA) and cysteine.

Enzymes which may be used as active agents with deep-down action are especially the DNA-repairing enzymes.

The active agents acting at the surface are chosen from keratolytic agents, tensioning agents, moisturizing agents, surface-restructuring agents and anti-free-radical agents.

Keratolytic agents acting at the surface which may be mentioned are α-hydroxy acids such as lactic acid, salicylic acid and 5-n-octanoylsalicylic acid.

Tensioning agents which may be mentioned are protein hydrolysates (for example of soya protein), such an those marketed by the company Silab under the reference Tensine.

Surface-restructuring agents which may be mentioned are peptide extracts from soya or from collagen, such an those marketed by the company Coletica under the reference Neptigene II.

As moisturizing agents acting at the surface, it impossible to use the same active agents as those with deep-down action mentioned above.

Anti-free-radical agents which may be mentioned are tocopherol (vitamin E) and the derivatives thereof (acetate), superoxide dismutases, ethoxyquin, guanosine, lactoperoxidase, glutathione peroxidase, and plant extracts having anti-free-radical activity, such as the aqueous extract of wheat germ marketed by the company Silab under the reference Detoxiline.

The agents active at the surface and the agents with deep-down action may be present in an amount of from 0.02 to 10% by weight, preferably 0.1 to 5% by weight, based on the total weight of the composition. In addition, the two categories of vesicles may contain other cosmetic active agents such an trace elements, sugars, etc.

The compositions according to the present invention may be provided in all the pharmaceutical forms normally used for topical application, such an aqueous gels, emulsions, lotions, ointments, sera and, more particularly, vesicle-dispersed oil droplets such as those described in French patents FR-A-2,485,921 and FR-A-2,490,504.

As is known, in addition to the vesicles, a vegetable oil, mineral oil, silicone-containing oil or synthetic oil which is dispersed in an aqueous phase, and also hydrophilic adjuvants such as gelling agents, antioxidants, preserving agents, opacifying agents, lipophilic adjuvants such as essential oils and fragrances, pigments and fillers, may be found in the compositions of the present invention, an described in the above French patents. For example, polyethylene beads may be added to provide a cleaning action (scrub). The dispersed oil may be present in an amount of from 2 to 40% by weight, preferably 5 to 20% by weight, based on the total weight of the composition, and the adjuvants may be present in a total amount of from 0.1 to 10% by weight, preferably 1 to 5% by weight, based on the total weight of the composition.

The present invention also relates to a use of the composition defined above for the preparation of an ointment intended to combat ageing and to a process for combating ageing, by applying this composition to the skin.

The vesicles of both the first and second types suitably comprise 1 to 90% by weight, preferably 5 to 70% by weight, more preferably 5 to 20% by weight, of the total weight of the composition.

The relative amounts of the vesicles of the first and second types in the present compositions are suitably:

10 to 90% by weight of the vesicles of the first type, and
90 to 10% by weight of the vesicles of the second type, preferably:

30 to 70% by weight of the vesicles of the first type, and
70 to 30% by weight of the vesicles of the second type,
based on the total weight of the vesicles of the first and second types.

Other features of the invention will become more apparent in the course of the following descriptions of exemplary embodiments which are given for illustration of the invention and are not intended to be limiting thereof.

EXAMPLES

In all of the Examples, the term "qs 100 g" means that that ingredient is present in an amount sufficient so that the sum of the amounts of all ingredients is 100 g.

A. Production of Lipid Vesicles Containing ASL

The constituent lipids of the wall of the vesicles are weighed out and dissolved in 10 ml of methanol. The alcoholic solution is than transferred into a 50 ml round-bottomed flask with a ground joint, which in subsequently placed on a rotary evaporator such that the contents are thermostatted at a temperature of 30° C. The evaporation in continued until a dry film of lipids in deposited on the wall of the flask.

3 ml of an aqueous 0.01 molar solution of ASL are then added to the flask, which in subsequently shaken by hand for about 10 minutes, either at room temperature (20° C.) for the vesicles of Table I of reference Nos. 7 to 10, or at a temperature of 50° C. for the vesicles of reference Nos. 1 to 6 of Table 1. The medium is then left to equilibrate at room temperature for 2 hours, then the dispersion is placed in a dialysis bag and in contact with 500 ml of distilled water. Dialysis in carried out overnight. The next day, the water is changed and the dialysis in continued for a further 4 hours.

A cotton thread 0.3 mm thick in then soaked in the vesicle dispersion and then placed in contact with a section of skin cut from a pig's ear which has been freshly recovered in an abattoir intended for food supply.

The ear sample taken is rinsed with water and cut into slices 1 mm thick, 5 mm wide and 10 mm long and then placed in a maintenance cell. Measurements of the diffusion of ASL in the skin are made in the 24 hours following the taking of the skin sample.

B. Production of the Cosmetic Composition

1. Production of Vesicles of the First Type (Diffusing Deep-Down)

The vesicles (with deep-down action) are prepared according to a usual method for co-fusion of the various membrane constituents (see Table I) chosen. Thus, the membrane constituent having the lowest melting point, $T_m$, is melted. The other membrane constituents are added thereto, including the active agents, and the mixture in then homogenized with moderate stirring and in finally partially hydrated, while maintaining the melting temperature, $T_m$, defined above.

An aqueous solution of at least one first active agent for the deep-down treatment in added to the paste obtained. The mixture is stirred with a turbine for 1 hour and 30 minutes in order to hydrate fully, while maintaining the temperature $T_m$. One or more other active agents for the deep-down treatment are added to the reaction medium, homogenization in carried out, and the temperature of the medium is lowered to room temperature (20° C.).

2. Production of Vesicles of the Second Type (Diffusing at the Surface)

An aqueous solution of a (or some) second active agent for the surface treatment in introduced, at room temperature (20° C.) and with simple stirring, into the chosen mixture of constituents which are to form the membrane of the vesicles acting at the surface (see Table I). Vesicles acting at the surface encapsulating the second active agent acting at the surface are thus obtained.

3. Production of the "Double-Liposomes" Composition

The fatty phase (the oils) of the composition is added to the medium containing the vesicles with deep-down action, and it is dispersed (at room temperature) with stirring. The reaction medium obtained is then mixed with that containing the vesicles acting at the surface. The adjuvants, such as preserving agents, a gelling agent which may be neutralized if necessary with a base (triethanolamine or sodium hydroxide), and fragrances, etc., are then optionally added.

The product obtained is in the form of a soft and smooth white cream which may be used in the cosmetic and/or dermatological field depending on the nature of the active agents (active at the surface and with deep-down action) chosen.

Specific examples of cosmetic compositions in accordance with the present invention are given below.

Example 1: Anti-Wrinkle Double-Liposome Cream

| Preparation A: Liposomes with deep-down action: | |
|---|---|
| PEG 8 stearate/cholesterol/sodium acylglutamate in a 47.5/47.5/5 weight ratio | 11.26 g |
| Tocapherol acetate | 1.00 g |
| Glycerine | 5.63 g |
| Soya protein hydrolysate (active agent) | 0.37 g |
| Disodium salt of ethylenediaminetetraacetic acid (sequestering agent) | 0.19 g |
| Demineralized water qs | 100 g |
| Preparation B: Liposomes acting at the surface: | |
| Natipide II marketed by the company Nattermann | 33.33 g |
| Glycerine (active agent) | 33.33 g |
| Native marine collagen (active agent) | 8.33 g |
| Demineralized water qs | 100 g |
| Double-liposome composition: | |
| Preparation A | 26.65 g |
| Preparation B | 9.00 g |
| Vegetable oil | 16.40 g |
| Volatile silicone oil | 4.00 g |
| Retinyl palmitate | 0.6 g |
| Fragrance | 0.4 g |
| Citric acid | 0.02 g |
| Microspheres of vinylidene chloride copolymer | 0.20 g |
| Preserving agents | 1.18 g |
| Carboxyvinyl polymer (gelling agent) | 0.50 g |
| Sodium hydroxide | 0.15 g |
| Demineralized water qs | 100 g |

Example 2: Anti-Free-Radical Double-Liposome Cream

| Preparation A: Liposomes with deep-down action: | |
|---|---|
| PEG 8 stearate/cholesterol/sodium acylglutamate in a 47.5/47.5/5 weight ratio | 10.33 g |
| alpha-Tocapherol | 1.00 g |
| Glycerine | 13.77 g |
| Guanosine | 0.30 g |
| Disodium salt of ethylenediamine-tetraacetic acid (active agent) | 0.17 g |
| Demineralized water qs | 100 g |
| Preparation B: Liposomes acting at the surface: | |
| Natipide II marketed by the company Nattermann | 35.29 g |
| Aqueous extract of wheat germ (active agent) marketed by the company Silab under the name Detoxiline | 5.88 g |
| Glycerine | 35.30 g |
| Demineralized water qs | 100 g |
| Double-liposome composition: | |
| Preparation A | 29.05 g |
| Preparation B | 8.50 g |
| Vegetable oil | 20.50 g |
| Volatile silicone oil | 3.50 g |
| Fragrance | 0.40 g |
| Citric acid | 0.02 g |
| Preserving agents | 1.18 g |
| Carboxyvinyl polymer (gelling agent) | 0.50 g |
| Sodium hydroxide | 0.15 g |
| Demineralized water qs | 100 g |

Example 3: Anti-Ageing Double-Liposome Cream

Preparation A: Liposomes with deep-down action:

| | |
|---|---|
| PEG 8 stearate/cholesterol/sodium acylglutamate in a 47.5/47.5/5 weight ratio | 11.52 g |
| Glycerine | 5.76 g |
| Disodium salt of ethylenediaminetetraacetic acid (sequestering agent) | 0.19 g |
| Mixture of alpha-hydroxy acids from fruit (lactic acid/glycolic acid/citric acid: 35/15/8) (active agent) | 1.92 g |
| Demineralized water qs | 100 g |

Preparation B: Liposomes acting at the surface:

| | |
|---|---|
| Natipide II marketed by the company Nattermann | 35.29 g |
| Lactic acid (active agent) | 5.88 g |
| Demineralized water qs | 100 g |

Double-liposome composition:

| | |
|---|---|
| Preparation A | 26.05 g |
| Preparation B | 8.50 g |
| Vegetable oil | 17.00 g |
| Volatile silicone oil | 4.00 g |
| Fragrance | 0.40 g |
| Preserving agents | 1.18 g |
| Carboxyvinyl polymer (gelling agent) | 0.50 g |
| Sodium hydroxide | 0.15 g |
| Demineralized water qs | 100 g |

Example 4: Anti-Ageing Double-Liposome Cream

Preparation A: Liposomes with deep-down action:

| | |
|---|---|
| PEG 8 stearate/cholesterol/sodium-acylglutamate in a 47.5/47.5/5 weight ratio | 11.26 g |
| Tocopherol acetate | 0.37 g |
| 5-n-Octanoylsalicylic acid (active agent) | 0.37 g |
| Glycerine | 5.63 g |
| Disodium salt of ethylenediaminetetraacetic acid | 0.19 g |
| Demineralized water qs | 100 g |

Preparation B: Liposomes acting at the surface:

| | |
|---|---|
| Natipide II marketed by the company Nattemamm | 36.58 g |
| Salicylic acid (active agent) | 2.44 g |
| Glycerine | 36.6 g |
| Demineralized water qs | 100 g |

Double-liposome composition:

| | |
|---|---|
| Preparation A | 26.65 g |
| Preparation B | 8.20 g |
| Vegetable oil | 17.00 g |
| Volatile silicone oil | 4.00 g |
| Fragrance | 0.40 g |
| Citric acid | 0.02 g |
| Preserving agents | 1.70 g |
| Carboxyvinyl polymer (gelling agent) | 0.50 g |
| Sodium hydroxide | 0.15 g |
| Demineralized water qs | 100 g |

This application is based on French Patent Application 93-15867 filed on Dec. 30, 1993, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the United States is:

1. A composition for combating ageing of the skin, which acts simultaneously on the layers of the stratum corneum and deep layers of the skin, comprising a dispersion mixture of:
   (a) a first dispersion of lipid vesicles which are capable of penetrating into said deep layers of the skin and which contain at least one skin antiageing agent having activity in the deep layers of the skin for treating said deep layers; and
   (b) a second dispersion of lipid vesicles which are capable of penetrating into said layers of the stratum corneum of the skin and which contain at least one skin antiageing agent having activity in the layers of the stratum corneum of the skin for treating said layers of the stratum corneum,
   and wherein said vesicles of said first dispersion ensure a distribution of N-(1-oxyl-2,2,6,6-tetramethyl-4-piperidyl)-N-dimethyl-N-hydroxyethylammonium iodide (ASL) in the stratum corneum $>1\times10^{-7}$ cm$^2$/s and in that said vesicles of said second dispersion ensure a distribution of ASL in the stratum corneum $<1\times10^{-7}$ cm$^2$/s.

2. The composition of claim 1, wherein said vesicles of said first dispersion are in a fluid state at room temperature and said vesicles of said second dispersion are in a gelled state at room temperature.

3. The composition of claim 1, wherein said vesicles of said first dispersion exhibit an encapsulation potential of glucose for at least 24 hours, and said vesicles of said second dispersion exhibit an encapsulation potential of glucose for less than 24 hours.

4. The composition of claim 1, wherein said vesicles of said first dispersion are formed of lipids having at least one linear and saturated fatty chain having from 16 to 30 carbon atoms.

5. The composition of claim 1, wherein said vesicles of said first dispersion are formed of at least one lipid selected from the group consisting of hydrogenated natural phospholipids, saturated synthetic phospholipids, polyol alkyl ethers having at least one linear fatty chain, polyol alkyl esters having at least one fatty chain, and mixtures thereof.

6. The composition of claim 1, wherein said vesicles of said first dispersion are formed of at least one lipid selected from the group consisting of: triglyceryl cetyl ether, cholesterol, and casein lipoamino acid; mixtures of triglyceryl mono-, di- and tricetyl ether, cholesterol, and dicetyl phosphate; triglyceryl cetyl ether, cholesterol, and dicetyl phosphate; sorbitan palmitate, cholesterol, and sodium acylglutamate; PEG 8 stearate, cholesterol, and sodium acylglutamate; Diglyceryl distearate, cholesterol, and sodium acylglutamate; sucrose mono- and distearate, cholesterol, and sodium acylglutamate; PEG 8 stearate, cholesterol, phytanetriol, and sodium acylglutamate; polyoxyethylenated methylglucose distearate containing 20 mol of ethylene oxide, cholesterol, and sodium acylglutamate; hydrogenated lecithin, and polyoxyethylenated phytosterol; and tetraglyceryl tristearate, cholesterol, and sodium acylglutamate.

7. The composition of claim 1, wherein said vesicles of said second dispersion are formed of lipids selected from the group consisting of natural ionic phospholipids having unsaturated fatty chains having from 16 to 30 carbon atoms, polyol alkyl ethers or polyol alkyl esters having one or more fatty chains per molecule, comprising at least one fatty chain with a length of less than 16 carbon atoms, and mixtures thereof.

8. The composition of claim 1 wherein said vesicles of said second dispersion are formed of at least one lipid selected from the group consisting of: sunflower lecithin; soya lecithin, ethanol, and water; soya lecithin, cholesterol, and propylene glycol; and lauryl polyglyceryl-6-cetearyl glycol ether and dimyristyl phosphate.

9. The composition of claim 1, wherein said active agent of said first dispersion and said active agent of said second dispersion provide the same function, the same effect or both.

10. The composition of claim 1, wherein said active agent of said first dispersion and said active agent of said second dispersion are the same.

11. The composition of claim 1, wherein said active agent contained in said first dispersion is selected from the group consisting of glycerine, phosphonic acid derivatives, ethylenediaminetetraacetic acid and salts thereof, α-hydroxy acids and salts thereof, salicylic acid derivatives, peptide derivatives, protein hydrolysates, polyunsaturated phospholipids, tocopherol and derivatives thereof, retinol and derivatives thereof, superoxide dismutases, guanosine, lactoperoxidase, and lactoferrin.

12. The composition of claim 1, wherein said active agent contained in said second dispersion is selected from the group consisting of salicylic acid and derivatives thereof, α-hydroxy acids, protein hydrolysates, collagen derivatives, glycerine, tocopherol and derivatives thereof, superoxide dismutases, ethoxyquin, guanosine, and lactoperoxidase.

13. The composition of claim 1, further comprising:

c) an oily phase dispersed in an aqueous phase.

14. The composition of claim 1, further comprising:

(d) a hydrophilic or lipophilic adjuvant.

15. A method for treating ageing of the skin, comprising applying to the skin of a subject in need thereof an effective amount of a composition, comprising a dispersion mixture of:

(a) a first dispersion of lipid vesicles which are capable of penetrating into deep layers of the skin and which contain at least one antiageing agent having activity in the deep layers of the skin for treating said deep layers; and (b) a second dispersion of lipid vesicles which are capable of penetrating into layers of the stratum corneum of the skin and which contain at least one antiageing agent having activity in the layers of the stratum corneum of the skin for treating said layers of the stratum corneum, and wherein said vesicles of said first dispersion ensure a distribution of N-(1-oxyl-2,2,6,6-tetramethyl-4-piperidyl)-N-dimethyl-N-hydroxyethylammonium iodide (ASL) in the stratum corneum $>1\times10^{-7}$ cm$^2$/s and in that said vesicles of said second dispersion ensure a distribution of ASL in the stratum corneum $<1\times10^{-7}$ cm$^2$/s.

16. The composition of claim 1, wherein said active agent contained in said first dispersion is 5-n-octanoylsalicylic acid.

17. The composition of claim 1, wherein said active agent contained in said second dispersion is 5-n-octanoylsalicylic acid.

* * * * *